United States Patent
Butler

(10) Patent No.: US 10,672,506 B2
(45) Date of Patent: Jun. 2, 2020

(54) METHOD AND DEVICE FOR GENERATING A GRAPHICAL USER INTERFACE FOR PROCEDURE-BASED MEDICAL CHARGE CAPTURE

(71) Applicant: William E. Butler, Boston, MA (US)

(72) Inventor: William E. Butler, Boston, MA (US)

(73) Assignee: Square Knot Systems, Inc., Cambridge, MA (US)

( * ) Notice: Subject to any disclaimer, the term of this patent is extended or adjusted under 35 U.S.C. 154(b) by 127 days.

(21) Appl. No.: 13/872,748

(22) Filed: Apr. 29, 2013

(65) Prior Publication Data

US 2013/0290026 A1     Oct. 31, 2013

Related U.S. Application Data

(60) Provisional application No. 61/639,209, filed on Apr. 27, 2012.

(51) Int. Cl.
G16H 50/70 (2018.01)
G16H 10/60 (2018.01)
G06F 19/00 (2018.01)

(52) U.S. Cl.
CPC ........... G16H 10/60 (2018.01); G06F 19/328 (2013.01)

(58) Field of Classification Search
CPC ...... G06Q 40/02; G06Q 30/04; G06F 19/325; G16H 10/60; G16H 50/70

USPC ........................................................ 705/2, 34
See application file for complete search history.

(56) References Cited

U.S. PATENT DOCUMENTS

| | | | | |
|---|---|---|---|---|
| 5,325,293 | A * | 6/1994 | Dorne ............................... | 705/2 |
| 5,557,514 | A * | 9/1996 | Seare ..................... | G06Q 40/02 705/2 |
| 5,970,463 | A * | 10/1999 | Cave et al. ....................... | 705/3 |
| 2002/0120466 | A1 * | 8/2002 | Finn ....................... | G06F 19/328 705/2 |
| 2002/0147615 | A1 * | 10/2002 | Doerr .................... | G06F 19/325 705/2 |
| 2004/0095382 | A1 * | 5/2004 | Fisher ................... | G06F 9/4451 715/744 |
| 2005/0125320 | A1 * | 6/2005 | Boesen .................. | G06Q 30/04 705/34 |
| 2005/0137910 | A1 * | 6/2005 | Rao ........................ | G06Q 10/10 705/3 |
| 2013/0144651 | A1 * | 6/2013 | Rao ........................ | G06Q 10/00 705/3 |

* cited by examiner

*Primary Examiner* — John A Pauls
(74) *Attorney, Agent, or Firm* — BakerHostetler

(57) ABSTRACT

A method and device for reducing a complexity of procedure based medical charge capture and coding utilizing a computer system. The method and device including searching for previously generated coding scenarios associated with the provider, using existing coding scenarios or adding coding scenarios to a library, generating and filtering codes associated with at least one of the steps of searching, using, and adding, formatting a graphical user interface specification to use the codes from the generating and filtering step, and storing the graphical user interface for presentation.

20 Claims, 5 Drawing Sheets

Cluster 1

| Freq | Code |
|---|---|
| 17 | I225.1 |
| 17 | C69990 |
| 16 | C61520 |
| 15 | C20926 |

Cluster 2

| Freq | Code |
|---|---|
| 17 | I225.2 |
| 17 | C61795 |
| 17 | C61512 |
| 2 | C69990 |
| 2 | C20926 |
| 2 | C62272 |

Cluster 3

| Freq | Code |
|---|---|
| 11 | C61751 |
| 5 | I348.8 |
| 3 | I239.6 |
| 2 | I331.3 |
| 2 | I191.1 |

Cluster 4

| Freq | Code |
|---|---|
| 9 | C61795 |
| 8 | C61510 |
| 3 | I191.1 |

Figure 4

Posterior Fossa for Acoustic Neuroma

ICD
- ☐ 225.1 Benign Tumor of Brain : Cranial nerves (include vestibular schwannoma aka acoustic neuroma)

CPT
- ☐ 61520 Craniectomy for excision of brain tumor, infratentorial or posterior \ fossa; cerebellopontine angle tumor
- ☐ 20926 Tissue grafts, other (eg, paratenon, fat, dermis)
- ☐ 69990 Microdissection Hydrocephalus
- ☐ 331.3 Communicating hydrocephalus
- ☐ 331.4 Obstructive hydrocephalus
- ☐ 61210 Placement external ventricular drain through bur hole

Figure 5

METHOD AND DEVICE FOR GENERATING A GRAPHICAL USER INTERFACE FOR PROCEDURE-BASED MEDICAL CHARGE CAPTURE

CROSS-REFERENCE TO RELATED APPLICATIONS

This application claims priority to and is a non-provisional of U.S. Provisional Patent application No. 61/639,209 filed Apr. 27, 2012; and is related to U.S. patent application Ser. No. 11/236,211 filed Sep. 26, 2005 both incorporated herein by reference in their entirety.

BACKGROUND OF THE INVENTION

The invention is in the technical field of surgery charge capture and billing software, processes, and devices. In particular, the invention is in the technical field of the generation of visual components on a computer graphical user interface in a manner that reduces the complexity of surgery charge capture.

When a medical service is provided by a physician, to compose a bill the diagnosis and service must be described ("coded") with accepted diagnosis and services codes. A common system of diagnosis codes in current use is the International Classification of Disease, version 9 (ICD-9), provided by the World Health Organization. A common system of service codes is Common Procedural Terminology (CPT), provided by the American Medical Association.

For charge capture and coding purposes, medical services may be categorized into Evaluation and Management (E & M) and Procedure Services. The Procedure Services include Surgical Services, wherein there is an invasive component. The E & M services generally include a face-to-face encounter between a physician and a patient that may include discussion, ordering of further diagnostic testing, or a prescription for a medicine. There are approximately 30 E & M CPT codes. This is few enough for the codes to be placed on one or several screens by an E & M software program for charge capture, where they may be combined with ICD-9 codes to complete the coding for a medical service bill. There are a number of commercial and noncommercial software programs that offer this functionality.

A Procedure Service, such as a surgery, commonly requires a combination of multiple CPT codes and multiple ICD-9 codes to describe it completely and accurately. There are in excess of 7,500 CPT codes for Procedure and Surgical Services and there are in excess of 5,000 ICD-9 codes. Thus, the combinatorial number of ICD-9 and CPT code combinations is thus very large, and has overwhelmed in its magnitude and complexity attempts to construct a graphical user interface that covers the procedure coding possibilities.

Accordingly, there is a need for reducing the complexity of graphical user interfaces for charge capture in Surgical Services.

SUMMARY OF THE INVENTION

The invention is a process and device for generating graphical user interface screens for charge capture in Surgical Services by using statistical methods drawn from the area of cluster analysis to reduce the complexity of Surgical Service Coding.

In one aspect of the invention, a method of reducing a complexity of procedure based medical charge capture and coding utilizing a computer system includes searching for previously generated coding scenarios associated with the provider, using existing coding scenarios or adding coding scenarios to a library, generating and filtering codes associated with at least one of the steps of searching, using, and adding, formatting a graphical user interface specification to use the codes from the generating and filtering step, and storing the graphical user interface for presentation.

Another aspect of the invention is a tangible non-transitory computer readable medium comprising instructions for reducing a complexity of procedure based medical charge capture and coding utilizing implemented on a computer system includes instructions for searching for previously generated coding scenarios associated with the provider, instructions for using existing coding scenarios or adding coding scenarios to a library, instructions for generating and filtering codes associated with at least one of the steps of searching, using, and adding, instructions for formatting a graphical user interface specification to use the codes from the generating and filtering step, and instructions for storing the graphical user interface for presentation.

In yet another aspect of the invention a device for reducing a complexity of procedure based medical charge capture and coding utilizing implemented includes means for searching for previously generated coding scenarios associated with the provider, means for using existing coding scenarios or adding coding scenarios to a library, means for generating and filtering codes associated with at least one of the steps of searching, using, and adding, means for formatting a graphical user interface specification to use the codes from the generating and filtering step, and means for storing the graphical user interface for presentation.

The invention includes a number of phases as described below. There is an enrollment phase where the medical claim history containing the ICD-9 and CPT codes may be gathered in an electronic file. The claim history may be obtained from the Provider in order to generate a simplified graphical user interface using the methods described herein. The claim history contains codings for many procedures where the coding was performed by hand without the benefit of this invention. The claim history is taken to represent a procedure pattern for the Provider likely to continue into the future.

A cluster analysis is performed on the codes in the claim history. This identifies which ICD-9 and CPT codes commonly co-occur or cluster in claims. These clusters are recorded for subsequent use in the translation phase as described below. A cluster may be given a convenient name for selection in a graphical user interface. This constitutes training of this charge capture software system for that Provider. In this patent application, the term "Provider" refers to an individual medical or surgical provider or group of providers (such as from the same surgical specialty) for whom the range of Surgical Services is suitably represented by the claim history used for cluster analysis.

There is a translation phase where the set of codes in a cluster derived from this analysis are translated into computer instructions for rendering a graphical user interface, and for capturing user input and merging this information into other information in this and other software programs for medical workflow, charge capture, and billing. The collection of graphical user interface widgets for a cluster is termed in this system a Scenario. A Scenario may be computed automatically, for example using rules to attach a checkbox widget to a given ICD-9 code which, when checked, indicates that that ICD-9 code is to be included in the claim to be forwarded to the payor. Or a Scenario may undergo editing a rearrangement by a human analyst to enhance its esthetic or usability value. The Scenarios are stored in the software system, and may be offered as forms to a Provider or designee when a medical or surgical service is being coded.

In the deployment phase, a Provider logs into the charge capture software using this system after performing a medical or surgical procedure. Having been trained by a file of claims that represent the Provider's practice pattern, the graphical user interface of this system can offer the Provider a convenient list of Coding Scenarios, each resulting from a statistical analysis in the enrollment phase, that cover to a statistical criterion, the practice pattern of the Provider. The Provider selects the Coding Scenario, and selects within the ICD-9 and CPT codes that best match the medical or surgical service provided. These codes populate an electronic claim, which, after possible review by other administrative specialists, may be forwarded to the payor.

The use of cluster analysis of historical claims to produce visual Coding Scenarios that reduce the complexity of a coding graphical user interface is a novel, non-obvious, and useful advance in the field.

Additional features, advantages, and embodiments of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 3 contains the first 10 lines of an example file of training codes for a particular surgeon (who happens to be a neurosurgeon) according to an aspect the invention;

FIG. 4 depicts the clusters from the analysis of the training set of FIG. 3 according to an aspect the invention; and FIG. 5 is the rendered Coding Scenario on a graphical user interface according to an aspect of the invention.

DETAILED DESCRIPTION OF THE INVENTION

Figure 1:
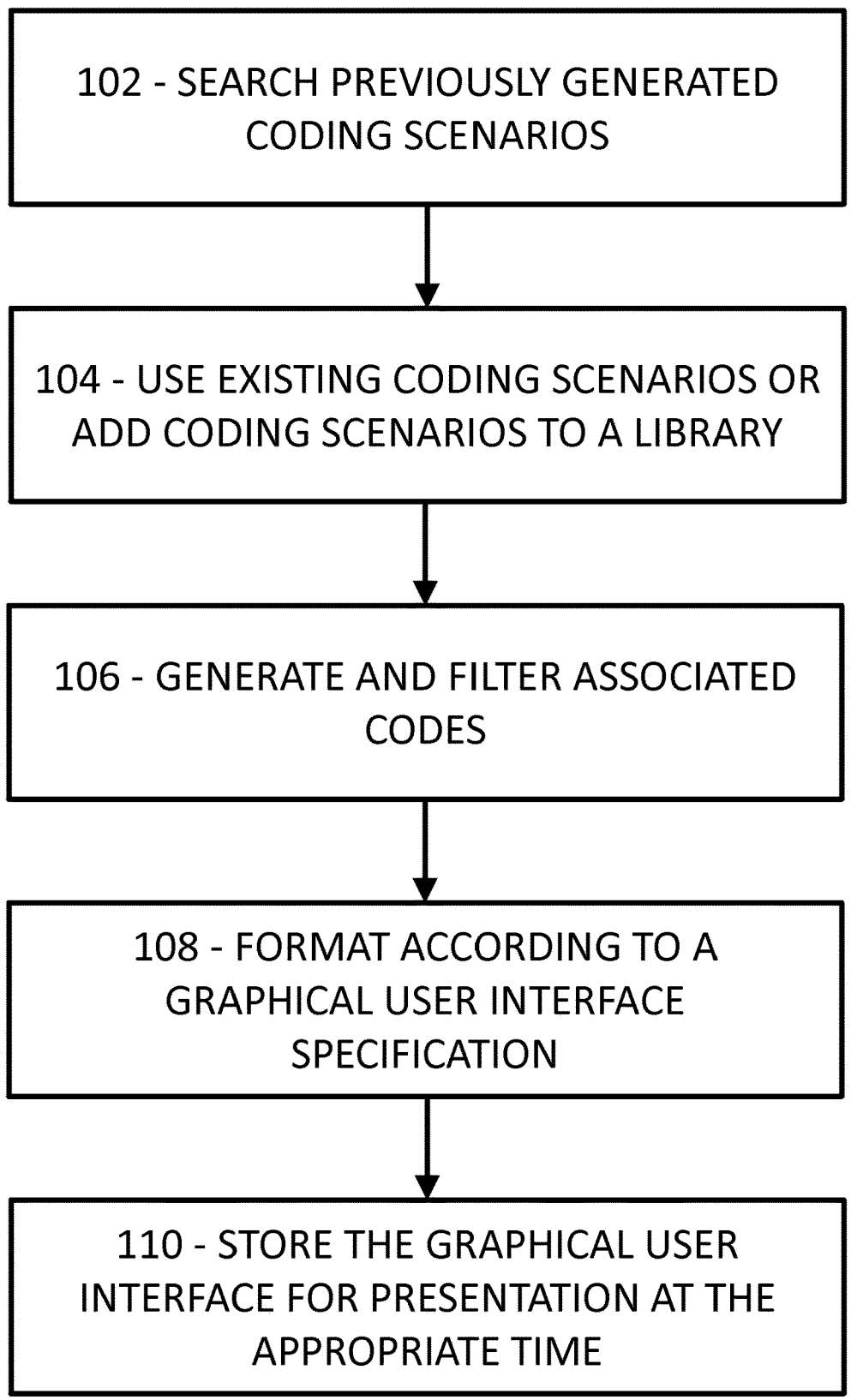
FIG. 1 is a flowchart of an aspect of the invention.

The aspects of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

FIG. 1 is a flowchart of an aspect of the invention. As shown in FIG. 1, when a Provider elects to use this system the enrollment phase starts with a search of library of previously generated Coding Scenarios 102 to see if existing ones match closely the practice pattern of the Provider to be enrolled. For example, if an orthopedic trauma specialist elects to use this system and there are already orthopedic trauma specialists using it, their set of Coding Scenarios may closely match the practice of the initiating provider such that no new custom Coding Scenarios need to be generated. Conversely, all new Coding Scenarios are added to a library for potential use by Provider other than those for whom the Coding Scenarios were generated 104.

If the library of existing Coding Scenarios does not suitably match the Provider to be enrolled, then a representative list of historical claims for that Provider going back six or twelve months is selected for analysis. While in this document the singular noun Provider is employed, the same techniques work for a group of Providers with similar practice pattern, such as a group of orthopedic trauma specialists who share a call schedule.

Figure 3:
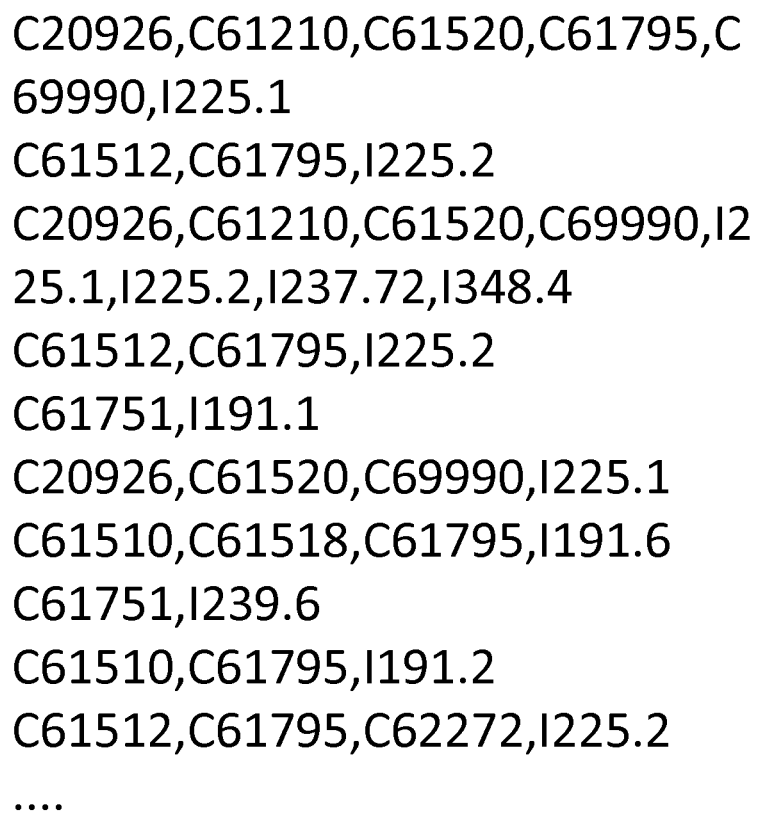

FIG. 3 contains the first 10 lines of an example file of training codes for a particular surgeon (who happens to be a neurosurgeon) according to the invention. Referring now to the invention in more detail, in FIG. 3 the list of training claims is placed in a file such that each line represents one claim, and on each line the ICD-9 and CPT codes are comma delimited. For clarity, the ICD-9 codes are prepended with "I" and the CPT codes with "C."

ICD-9 and CPT and the most commonly used code systems in the United States today. There are other coding systems such as ICD-10 (scheduled to replace ICD-9 in the United States in October 2013), and Diagnosis Related Group (DRG). Moreover, there is a subset of ICD-9 and ICD-10 not in common use in 2010 that describes procedures. This subset, if adopted, would substitute for CPT. Those skilled in the art can see that the methods described in this document can be applied to other coding systems and biomedical ontologies (for a partial listing of these see http://www.bioontology.org/), but ICD-9 and CPT are selected for illustration in this document because at the time of this writing they the standard coding systems for medical charge capture in the United States of America.

In this invention the Mathematica (Wolfram Research, Urbana Ill.) computer programming language may be used to perform the cluster analysis. Those skilled in the art of cluster analysis will recognize that there are other programming languages and libraries well suited to this task, such as the R programming language (http://www.r-project.org/) or the like. In addition, there are many mathematical and statistical techniques for cluster analysis. In the course of performing the research that led to the invention, we have employed several programming languages and cluster library functions, and have assessed their pros and cons. For illustrative simplicity, we present in this application usage of the FindClusters function supplied by Mathematica. An example of source instructions in Mathematica for inputting a training file of claims, performing the cluster analysis, and outputting a Coding Scenario in HTML may be utilized as set forth in U.S. Provisional Patent application No. 61/639, 209 filed Apr. 27, 2012. Additionally, other types of cluster analysis are contemplated as well and are within the spirit and scope of the invention.

In particular, the cluster analysis finds associated combinations of codes. Thereafter, the associated combinations of codes may be mapped to a graphical user interface. The cluster analysis or clustering groups a set of codes in such a way that codes in the same group are similar to each other than to those in other groups. In this approach, the cluster analysis finds a more convenient combination of codes for the provider to utilize.

Each cluster generated by this program contains a list of ICD-9 and CPT codes, each with a measure of their strength of association with the cluster. Those codes strongly associated with a cluster are preserved for later rendering in in Coding Scenario for the graphical user interface. Typically, a cluster contains several codes that are weakly associated with the cluster. These codes may be excluded from the rendered Coding Scenario in order to keep it simple and therefore conveniently usable.

When a cluster of codes is generated and filtered to retain its more strongly associated codes 106, it is then formatted into computer instructions according to a graphical user interface specification 108, in this embodiment HTML. The HTML instructions may be inserted into a graphical user screen as a Coding Scenario as is, or it may be reviewed and modified by rules implemented in a computer, or by a human according to taste. An example of a computer-based rule modification is that if there are some codes known to be mutually exclusive, they may be rendered with a visual widget that enforces this such as a radio box, rather than as a list of checkboxes.

FIG. 5 is the rendered Coding Scenario on a graphical user interface according to an aspect of the invention. More specifically, FIG. 5 is the rendered Coding Scenario as translated by the invention from Cluster 1 in FIG. 4 to HTML code according to the invention (It contains an embedded Hydrocephalus Coding Scenario to illustrate the sub invention of hierarchical Coding Scenarios). Coding Scenarios may be hierarchically organized and thus may be embedded one within the other in the graphical user interface. FIG. 5 contains thus a snippet of rendered HTML for a Coding Scenario computed as per FIG. 2. The Coding Scenario in FIG. 5 is named "Posterior Fossa for Acoustic Neuroma," based on a human inspect of the rendered codes. In addition, for illustration of a possible hierarchical Coding Group organization, it contains a hydrocephalus Coding Group, based a meta cluster analysis that shows that hydrocephalus Coding Group embedded within the Posterior Fossa Craniotomy for Acoustic Neuroma Coding Group.

As shown in FIG. 1, the HTML instructions for a Coding Scenario are then stored in a computer database and may be presented in the graphical user interface to the provider or other appropriate personnel at the appropriate time 110. The captured coding information may then be fused by this or a separate computer program with other information such as the patient's demographic and payor data, and then conveyed for payment.

Figure 2:
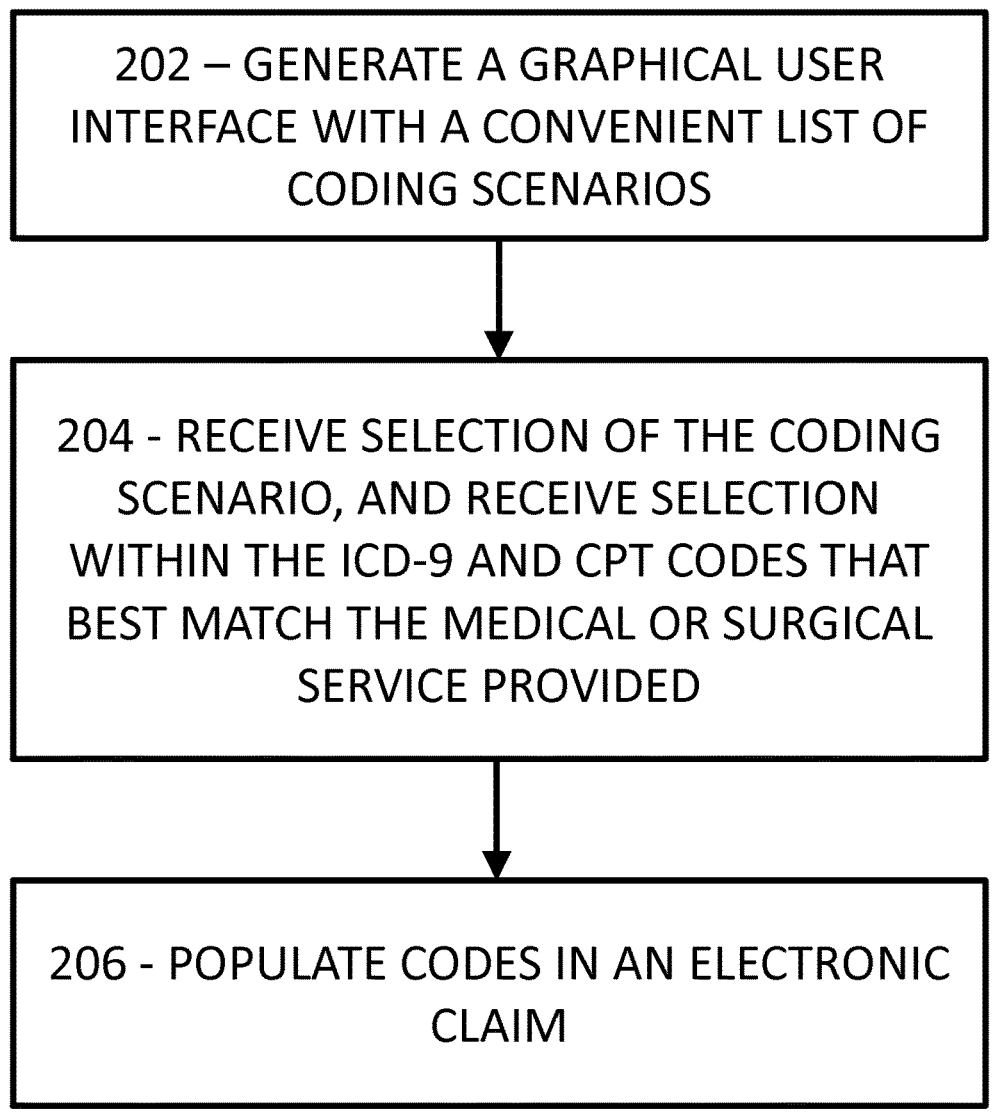
FIG. 2 is a flowchart of another aspect of the invention.

FIG. 2 is a flowchart of another aspect of the invention. Having been trained by a file of claims that represent the Provider's practice pattern, the graphical user interface of this system can offer the Provider a convenient list of Coding Scenarios 202, each resulting from a statistical analysis in the enrollment phase, that cover to a statistical criterion, the practice pattern of the Provider. The Provider selects the Coding Scenario, and selects within the ICD-9 and CPT codes that best match the medical or surgical service provided 204. These codes populate an electronic claim 206, which, after possible review by other administrative specialists, may be forwarded to the payor.

The advantages of the invention include, without limitation, the reduction of complexity in charge capture for procedure based medical services such as surgery, coupled with the custom generation for a Provider of a graphical user interface that is trained from that Provider's historical practice pattern.

This invention has been reduced to practice at Massachusetts General Hospital, where it is currently the foundation for the charge capture software for most surgical and other procedure based medical services. As of the filing of, there are approximately 998 Coding Scenarios generated for Providers in about 22 different medical and surgical specialties. The invention has been found to increase the adoption of computer methods for medical procedure workflow and charge capture by reducing the complexity of the graphical user interface. This has resulted in increased speed and accuracy of surgical workflow and charge capture.

The invention is a method for reducing the complexity of a graphical user interface designed for charge capture in procedure-based medicine. The method is to perform a statistical cluster analysis of that individual's history and transform the result into computer instructions for rendering a graphical user interface.

The steps involved in a medical service include "coding" it, meaning selecting the proper diagnosis and procedure codes, which are then placed on an invoice. Currently, in the United States the commonly used diagnostic coding system is ICD-9 and the procedure coding system is CPT. For consultation services (known and Evaluation and Management) there are approximately 30 CPT codes. This is tractable for placement on a computer graphical user interface. However, for procedure-based services such as surgery there are more than about 7,500 CPT codes. When combinatorially mixed with the more than 5,000 ICD-9 codes, the graphical user interface may be too complex for efficient and accurate use.

This invention stems from the recognition that these codes commonly occur in clusters. For example, the coding and claim history of an orthopedic trauma specialist may include a cluster of codes that cover the diagnosis and treatment of an arm fracture. Thus, this invention includes for a Provider an enrollment phase where a claim history is statistically analyzed for clusters. Then there is a translation phase where those clusters are translated into computer instructions for generating a graphical user interface. Each graphical user interface translated from a code cluster is termed here a Coding Scenario. The coding scenarios are stored in durable computer memory such as a database. There is a deployment phase where the appropriate Coding Scenarios are retrieved from the database and rendered on a computer screen for convenient interaction with a human user.

The description above of the invention enables one skill in the arts of computer statistical analysis and graphical user interface creation to make and use what is considered presently to be the best mode thereof. Those of skill in these arts will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), W-CDMA (Wideband Code-Division Multiple Access), Wireless Fidelity (Wi-Fi), Bluetooth, and/or the like, and/or a combination of two or more thereof.

The invention may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

In an embodiment, the invention may be web-based. For example, a server may operate a web application to allow the invention to operate in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™ or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

In an embodiment, the invention may be implemented in any type of mobile smartphones that are operated by any type of advanced mobile data processing and communication operating system, such as, e.g., an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system or the like.

Further in accordance with various embodiments of the invention, the methods described herein are intended for operation with dedicated hardware implementations including, but not limited to, PCs, PDAs, net book computers, tablet computers, iPad, semiconductors, application specific integrated circuits (ASIC), programmable logic arrays, cloud computing devices, and other hardware devices constructed to implement the methods described herein.

It should also be noted that the software implementations of the invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

The invention claimed is:

1. A method of reducing a complexity of procedure based medical charge capture and coding utilizing a medical charge capture and billing computer system comprising:

generating coding scenarios that comprise a plurality of medical diagnosis codes and medical service codes with the medical charge capture and billing computer system that include searching, receiving, and analyzing;

the searching comprising searching a medical charge capture and billing computer database library for existing previously generated coding scenarios that comprise a plurality of medical diagnosis codes and medical service codes associated with a specialty of a provider with the medical charge capture and billing computer system;

the receiving comprising receiving new coding scenarios that comprise a plurality of medical diagnosis codes and medical service codes with the medical charge capture and billing computer system;

the analyzing comprising selecting and analyzing historical claims for the provider with the medical charge capture and billing computer system to obtain coding scenarios that comprise a plurality of medical diagnosis codes and medical service codes;

the analyzing historical claims comprises: generating and filtering with the medical charge capture and billing computer system the obtained coding scenarios associated with the analyzing;

the generating and filtering comprises performing a statistical cluster analysis of the obtained coding scenarios with the medical charge capture and billing computer system to generate associated codes that comprise a plurality of medical diagnosis codes and medical service codes, the associated codes excluding codes from the coding scenarios that are associated with a cluster of the statistical cluster analysis;

formatting with the medical charge capture and billing computer system a medical charge capture and billing graphical user interface specification to use the associated codes from the generating and filtering step as coding scenarios;

storing the medical charge capture and billing graphical user interface in the medical charge capture and billing computer database for presentation of the coding scenarios to the provider;

implementing a medical charge capture and billing computer device that is configured to generate a graphical user interface that comprises the medical charge capture and billing graphical user interface specification configured to present the coding scenarios that comprise a plurality of medical diagnosis codes and medical service codes to the provider;

receiving a selection from a user of one of the coding scenarios in the medical charge capture and billing graphical user interface of the medical charge capture and billing computer device; and populating an electronic claim with a selected one of the coding scenarios that comprise a plurality of medical diagnosis codes and medical service codes with the medical charge capture and billing computer device in response to the receiving the selection from the user of one of the coding scenarios in the medical charge capture and billing graphical user interface of the medical charge capture and billing computer device.

2. The method according to claim 1 wherein:

the searching comprising searching a medical charge capture and billing computer database library for existing previously generated coding scenarios that comprise a plurality of medical diagnosis codes and medical service codes that match closely to a practice pattern of the provider associated with a specialty of the provider with the medical charge capture and billing computer system; and the formatting further comprises formatting the medical charge capture and billing graphical user interface for presentation by the medical charge capture and billing computer device that comprises at least one of the following: a server, a smart phone, a tablet computer, desktop, and a netbook.

3. The method according to claim 1 wherein:

the generating and filtering comprises performing a statistical cluster analysis of the obtained coding scenarios with the medical charge capture and billing computer system to generate associated codes that comprise a plurality of medical diagnosis codes and medical service codes further comprises finding associated combinations of codes; and the storing the medical charge capture and billing graphical user interface further comprises storing the medical charge capture and billing graphical user interface in a memory of the medical charge capture and billing computer device that comprises at least one of the following: a server, a smart phone, a tablet computer, desktop, and a netbook.

4. The method according to claim 1 further comprising:

displaying the medical charge capture and billing graphical user interface on a display of the medical charge capture and billing computer device, wherein the medical charge capture and billing graphical user interface is rendered in HTML as a webpage and displays the coding scenarios, wherein the medical diagnosis codes comprise International Classification of Disease (ICD) codes and the medical service codes comprise Common Procedural Terminology (CPT) codes.

5. The method according to claim 1 wherein:

the generating and filtering comprises performing a statistical cluster analysis of the obtained coding scenarios with the medical charge capture and billing computer system to generate associated codes that comprise a plurality of medical diagnosis codes and medical service codes further comprises mapping the associated codes to the graphical user interface; and the medical diagnosis codes comprise International Classification of Disease (ICD) codes and the medical service codes comprise Common Procedural Terminology (CPT) codes.

6. The method according to claim 1 wherein:

the performing a statistical cluster analysis of the obtained coding scenarios comprises identifying medical diagnosis codes and medical service codes that commonly cluster in medical claims; and the medical diagnosis codes comprise International Classification of Disease (ICD) codes and the medical service codes comprise Common Procedural Terminology (CPT) codes.

7. The method according to claim 1 wherein:

the performing a statistical cluster analysis of the obtained coding scenarios comprises generating a measure of a strength of association with the cluster that includes medical diagnosis codes and medical service codes that commonly cluster in medical claims; and the medical diagnosis codes comprise International Classification of Disease (ICD) codes and the medical service codes comprise Common Procedural Terminology (CPT) codes.

8. The method according to claim 1 wherein:

the performing a statistical cluster analysis of the obtained coding scenarios comprises retaining medical diagnosis codes and medical service codes that commonly cluster in medical claims that are associated with a cluster; and the medical diagnosis codes comprise International Classification of Disease (ICD) codes and the medical service codes comprise Common Procedural Terminology (CPT) codes.

9. The method according to claim 1 wherein the medical diagnosis codes comprise International Classification of Disease (ICD) codes and the medical service codes comprise Common Procedural Terminology (CPT) codes;

wherein the performing a statistical cluster analysis of the obtained coding scenarios comprises identifying medical diagnosis codes and medical service codes that commonly cluster in medical claims;

wherein the performing a statistical cluster analysis of the obtained coding scenarios comprises generating a measure of a strength of association with the cluster that includes medical diagnosis codes and medical service codes that commonly cluster in medical claims; and wherein the performing a statistical cluster analysis of the obtained coding scenarios comprises retaining medical diagnosis codes and medical service codes that commonly cluster in medical claims that are associated with a cluster.

10. The method according to claim 1 wherein:

the searching comprising searching a medical charge capture and billing computer database library for existing previously generated coding scenarios that comprise a plurality of medical diagnosis codes and medical service codes that match closely to a practice pattern of the provider associated with a specialty of the provider with the medical charge capture and billing computer system;

the generating and filtering comprises performing a statistical cluster analysis of the obtained coding scenarios with the medical charge capture and billing computer system to generate associated codes that comprise a plurality of medical diagnosis codes and medical service codes further comprises finding associated combinations of codes;

the generating and filtering comprises performing a statistical cluster analysis of the obtained coding scenarios with the medical charge capture and billing computer system to generate associated codes that comprise a plurality of medical diagnosis codes and medical service codes further comprises mapping the associated combinations of codes to the graphical user interface; and the generating and filtering comprises performing a statistical cluster analysis of the obtained coding scenarios with the medical charge capture and billing computer system to generate associated codes that comprise a plurality of medical diagnosis codes and medical service codes further comprises determining a measure of a strength of association with the cluster.

11. A tangible non-transitory computer readable medium comprising instructions for execution on a medical charge capture and billing computer system for reducing a complexity of procedure based medical charge capture and coding implemented on the medical charge capture and billing computer system comprising:

instructions for generating coding scenarios that comprise a plurality of medical diagnosis codes and medical service codes with the medical charge capture and billing computer system that include searching, receiving, and analyzing;

the searching comprising instructions for searching a medical charge capture and billing computer database library for existing previously generated coding scenarios that comprise a plurality of medical diagnosis codes and medical service codes associated with a specialty of a provider with the medical charge capture and billing computer system;

the receiving comprising instructions for receiving new coding scenarios that comprise a plurality of medical diagnosis codes and medical service codes with the medical charge capture and billing computer system;

the analyzing comprising instructions for selecting and analyzing historical claims for the provider with the medical charge capture and billing computer system to obtain coding scenarios that comprise a plurality of medical diagnosis codes and medical service codes;

the analyzing historical claims comprises: instructions for generating and filtering with the medical charge capture and billing computer system the obtained coding scenarios associated with the analyzing;

the instructions for generating and filtering further comprises instructions for performing a statistical cluster analysis of the obtained coding scenarios to generate associated codes that comprise a plurality of medical diagnosis codes and medical service codes, the associated codes excluding codes from the coding scenarios that are associated with a cluster of the statistical cluster analysis;

instructions for formatting with the medical charge capture and billing computer system a medical charge capture and billing graphical user interface specification to use the associated codes from the generating and filtering as coding scenarios;

instructions for storing with the medical charge capture and billing computer system the medical charge capture and billing graphical user interface in the medical charge capture and billing computer database for presentation of the coding scenarios to the provider;

instructions for implementing a medical charge capture and billing computer device that is configured to generate a graphical user interface that comprises the medical charge capture and billing graphical user interface configured to present the coding scenarios that comprise a plurality of medical diagnosis codes and medical service codes to the provider;

instructions for receiving a selection from a user of one of the coding scenarios in the medical charge capture and billing graphical user interface of the medical charge capture and billing computer device; and instructions for populating an electronic claim with a selected one of the coding scenarios that comprise a plurality of medical diagnosis codes and medical service codes with the medical charge capture and billing computer device in response to receiving the selection from the user of one of the coding scenarios in the medical charge capture and billing graphical user interface of the medical charge capture and billing computer device.

12. The computer readable medium according to claim 11 wherein:

the instructions for searching comprising searching a medical charge capture and billing computer database library for existing previously generated coding scenarios that comprise a plurality of medical diagnosis codes and medical service codes that match closely to a practice pattern of the provider associated with a specialty of the provider with the medical charge capture and billing computer system: and the instructions for formatting comprising instructions for formatting the medical charge capture and billing graphical user interface for operation with the medical charge capture and billing computer device that comprises at least one of the following: a server, a smart phone, a tablet computer, desktop, and a netbook.

13. The computer readable medium according to claim 7 wherein:

the instructions for generating and filtering comprises performing a statistical cluster analysis of the obtained coding scenarios with the medical charge capture and billing computer system to generate associated codes that comprise a plurality of medical diagnosis codes and medical service codes further comprises finding associated combinations of codes; and the instructions for storing the medical charge capture and billing graphical user interface further comprises instructions for storing the medical charge capture and billing graphical user interface in a memory of the medical charge capture and billing computer device that comprises at least one of the following: a server, a smart phone, a tablet computer, desktop, and a netbook.

14. The computer readable medium according to claim 11 further comprising:

instructions for displaying the medical charge capture and billing graphical user interface on a display of the medical charge capture and billing computer device, wherein the medical charge capture and billing graphical user interface is rendered in HTML as a webpage and displays the coding scenarios, wherein the medical diagnosis codes comprise International Classification of Disease (ICD) codes and the medical service codes comprise Common Procedural Terminology (CPT) codes.

15. The computer readable medium according to claim 11 wherein the medical diagnosis codes comprise International Classification of Disease (ICD) codes and the medical service codes comprise Common Procedural Terminology (CPT) codes;

wherein the performing a statistical cluster analysis of the obtained coding scenarios comprises identifying medical diagnosis codes and medical service codes that commonly cluster in medical claims;

wherein the performing a statistical cluster analysis of the obtained coding scenarios comprises generating a measure of a strength of association with the cluster that includes medical diagnosis codes and medical service codes that commonly cluster in medical claims; and wherein the performing a statistical cluster analysis of the obtained coding scenarios comprises retaining medical diagnosis codes and medical service codes that commonly cluster in medical claims that are associated with a cluster.

16. A medical charge capture and buffing system for reducing a complexity of procedure based medical charge capture and coding comprising:

a medical charge capture and billing computer system configured to generate coding scenarios that comprise a plurality of medical diagnosis codes and medical service codes that include searching, receiving, and analyzing;

the searching comprising the medical charge capture and billing computer system being configured to search for existing previously generated coding scenarios that comprise a plurality of medical diagnosis codes and medical service codes associated with a specialty of a provider;

the receiving comprising the medical charge capture and billing computer system being further configured to receive new coding scenarios that comprise a plurality of medical diagnosis codes and medical service codes;

the analyzing comprising the medical charge capture and billing computer system being further configured select and analyze historical claims for the provider with the medical charge capture and billing computer system to obtain coding scenarios that comprise a plurality of medical diagnosis codes and medical service codes;

the medical charge capture and billing computer system further configured to generate and filter the obtained coding scenarios;

the medical charge capture and billing computer system is further configured to perform a statistical cluster analysis of the obtained coding scenarios to generate associated codes that comprise a plurality of medical diagnosis codes and medical service codes, the associated codes excluding codes from the coding scenarios that are associated with a cluster of the statistical cluster analysis;

the medical charge capture and billing computer system further configured to format a medical charge capture and billing graphical user interface specification to use the associated codes;

the medical charge capture and billing computer system further configured to store the medical charge capture and billing graphical user interface for presentation of the coding scenarios to the provider;

a medical charge capture and billing computer device that is configured to generate a graphical user interface that comprises the medical charge capture and billing graphical user interface configured to present the coding scenarios that comprise a plurality of medical diagnosis codes and medical service codes to the provider;

the medical charge capture and billing computer device configured to receive a selection from a user of one the coding scenarios in the medical charge capture and billing graphical user interface; and the medical charge capture and billing computer device configured to populate an electronic claim with a selected one of the coding scenarios that comprise a plurality of medical diagnosis codes and medical service codes in response to the selection from the user of one the coding scenarios in the medical charge capture and billing graphical user interface.

17. The medical charge capture and billing system according to claim 16 wherein:

the medical charge capture and billing computer system further configured search a medical charge capture and billing computer database library for existing previously generated coding scenarios that comprise a plurality of medical diagnosis codes and medical service codes that match closely to a practice pattern of the provider associated with a specialty of the provider with the medical charge capture and billing computer system; and the medical charge capture and billing computer system is further configured to format the medical charge capture and billing graphical user interface for operation with the medical charge capture and billing computer device that comprises at least one of the following: a server, a smart phone, a tablet computer, desktop, and a netbook.

18. The medical charge capture and billing system according to claim 16 wherein:

the medical charge capture and billing computer system is further configured to find associated combinations of codes; and the medical charge capture and billing computer system is further configured to store the medical charge capture and billing graphical user interface in a memory of the medical charge capture and billing computer device that comprises at least one of the following: a server, a smart phone, a tablet computer, desktop, and a netbook.

19. The medical charge capture and billing device according to claim 16 wherein:

the medical charge capture and billing computer system is further configured to display the graphical user interface on a display of the medical charge capture and billing computer device;

the medical charge capture and billing graphical user interface is rendered in HTML as a webpage and displays the coding scenarios; and the medical diagnosis codes comprise International Classification of Disease (ICD) codes and the medical service codes comprise Common Procedural Terminology (CPT) codes.

20. The medical charge capture and billing system according to claim 16 wherein the medical diagnosis codes comprise International Classification of Disease (ICD) codes and the medical service codes comprise Common Procedural Terminology (CPT) codes;

wherein the performing a statistical cluster analysis of the obtained coding scenarios comprises identifying medical diagnosis codes and medical service codes that commonly cluster in medical claims;

wherein the performing a statistical cluster analysis of the obtained coding scenarios comprises generating a measure of a strength of association with the cluster that includes medical diagnosis codes and medical service codes that commonly cluster in medical claims; and wherein the performing a statistical cluster analysis of the obtained coding scenarios comprises retaining medical diagnosis codes and medical service codes that commonly cluster in medical claims that are associated with a cluster.

* * * * *

UNITED STATES PATENT AND TRADEMARK OFFICE
CERTIFICATE OF CORRECTION

PATENT NO. : 10,672,506 B2  
APPLICATION NO. : 13/872748  
DATED : June 2, 2020  
INVENTOR(S) : William E. Butler Page 1 of 1

It is certified that error appears in the above-identified patent and that said Letters Patent is hereby corrected as shown below:

In the Claims

Column 13 In Claim 16, Line 1:
"A medical charge capture and buffing system for" should be replaced with --A medical charge capture and billing system for--

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*